US009854975B2

(12) United States Patent
Van Pieterson et al.

(10) Patent No.: US 9,854,975 B2
(45) Date of Patent: Jan. 2, 2018

(54) SKIN MONITORING DEVICE, METHOD OF MONITORING THE SKIN, MONITORING DEVICE, METHOD OF IRRADIATING THE SKIN, AND USE OF AN OLED

(75) Inventors: Liesbeth Van Pieterson, Eindhoven (NL); Margreet De Kok, Eindhoven (NL); Sima Asvadi, Eindhoven (NL); Bernardus Hendrikus Wilhelmus Hendriks, Eindhoven (NL); Gerhardus Wilhelmus Lucassen, Eindhoven (NL); Jacqueline Van Driel, Drachten (NL); Paul Van Der Sluis, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1113 days.

(21) Appl. No.: 12/304,137

(22) PCT Filed: Jun. 11, 2007

(86) PCT No.: PCT/IB2007/052199
§ 371 (c)(1),
(2), (4) Date: Dec. 10, 2008

(87) PCT Pub. No.: WO2007/144817
PCT Pub. Date: Dec. 21, 2007

(65) Prior Publication Data
US 2009/0318908 A1 Dec. 24, 2009

(30) Foreign Application Priority Data
Jun. 12, 2006 (EP) .................................... 06115267

(51) Int. Cl.
*A61B 5/00* (2006.01)
*A61N 5/06* (2006.01)
*A61N 5/067* (2006.01)

(52) U.S. Cl.
CPC ............ *A61B 5/0059* (2013.01); *A61B 5/443* (2013.01); *A61B 5/445* (2013.01); *A61N 5/062* (2013.01);
(Continued)

(58) Field of Classification Search
CPC ....... A61B 5/0059; A61B 5/445; A61B 5/443; A61B 5/418; A61N 5/062; A61N 5/0616;
(Continued)

(56) References Cited

U.S. PATENT DOCUMENTS 5,435,307 A * 7/1995 Friauf et al. .................. 600/317
5,680,857 A 10/1997 Pelikan et al.
(Continued)

FOREIGN PATENT DOCUMENTS

EP 1384446 A 1/2004
JP 06254170 A 9/1994
(Continued)

OTHER PUBLICATIONS

Whelan et al, "The NASA Light-Emitting Diode Medical Program—Progress in Space Flight and Terrestrial Applications", American Institute of Physics, 2000, pp. 37-43.

*Primary Examiner* — Long V Le
*Assistant Examiner* — Angela M Hoffa

(57) ABSTRACT

Skin monitoring device for application near the skin includes a processing circuit and at least one photosensor configured to detect at least one approximate wavelength of light reflected and/or emitted by the skin. A signal receiving circuit receives signals from the photosensor.

19 Claims, 6 Drawing Sheets

(52) U.S. Cl.
CPC ............ *A61N 5/0616* (2013.01); *A61B 5/418* (2013.01); *A61N 2005/067* (2013.01); *A61N 2005/0629* (2013.01); *A61N 2005/0645* (2013.01)

(58) Field of Classification Search
CPC ...... A61N 2005/067; A61N 2005/0645; A61N 2005/0629
See application file for complete search history.

(56) References Cited

U.S. PATENT DOCUMENTS

| | | | | |
|---|---|---|---|---|
| 5,701,902 | A * | 12/1997 | Vari et al. | 600/473 |
| 5,779,631 | A * | 7/1998 | Chance | 600/328 |
| 5,853,370 | A * | 12/1998 | Chance et al. | 600/473 |
| 5,893,364 | A | 4/1999 | Haar et al. | |
| 6,032,071 | A * | 2/2000 | Binder | 600/476 |
| 6,240,309 | B1 * | 5/2001 | Yamashita et al. | 600/407 |
| 6,397,099 | B1 * | 5/2002 | Chance | 600/473 |
| 6,459,919 | B1 * | 10/2002 | Lys et al. | 600/407 |
| 6,553,242 | B1 | 4/2003 | Sarussi | |
| 6,663,659 | B2 | 12/2003 | McDaniel | |
| 7,072,700 | B2 * | 7/2006 | Yamamoto et al. | 600/310 |
| 7,439,484 | B2 * | 10/2008 | Liess et al. | 250/221 |
| 7,860,554 | B2 * | 12/2010 | Leonardi et al. | 600/473 |
| 7,920,249 | B2 * | 4/2011 | Heinks et al. | 356/5.09 |
| 7,942,869 | B2 * | 5/2011 | Houbolt et al. | 606/12 |
| 8,781,545 | B2 * | 7/2014 | De Kok | A61B 5/0059 600/323 |
| 2003/0088162 | A1 * | 5/2003 | Yamamoto et al. | 600/310 |
| 2004/0247484 | A1 | 12/2004 | Yerazunis | |
| 2005/0099824 | A1 | 5/2005 | Dowling et al. | |
| 2006/0173253 | A1 * | 8/2006 | Ganapathy et al. | 600/310 |
| 2006/0241495 | A1 * | 10/2006 | Kurtz | 600/476 |
| 2008/0188726 | A1 * | 8/2008 | Presura et al. | 600/322 |
| 2008/0312517 | A1 * | 12/2008 | Genoe et al. | 600/323 |
| 2009/0163819 | A1 * | 6/2009 | De Kok et al. | 600/476 |
| 2009/0204185 | A1 * | 8/2009 | De Kok et al. | 607/88 |

FOREIGN PATENT DOCUMENTS

| | | |
|---|---|---|
| JP | 09206283 A | 8/1997 |
| JP | 11326182 A | 11/1999 |
| JP | 2001112742 A | 4/2001 |
| JP | 2003169784 A | 6/2003 |
| JP | 2004511878 A | 4/2004 |
| JP | 2005521995 A | 7/2005 |
| JP | 2005265849 A | 9/2005 |
| RU | 2145247 C1 | 2/2000 |
| WO | 9608201 A1 | 3/1996 |
| WO | 0154770 A1 | 8/2001 |
| WO | WO 0237410 A1 * | 5/2002 |
| WO | 0237410 A1 | 10/2002 |
| WO | 03083818 A1 | 10/2003 |
| WO | 2004027402 A1 | 4/2004 |
| WO | 2006038168 A | 4/2006 |
| WO | WO 2006038168 A1 * | 4/2006 |
| WO | 2006082565 A1 | 8/2006 |
| WO | 2006085278 A2 | 8/2006 |
| WO | 2007054855 A1 | 5/2007 |

* cited by examiner

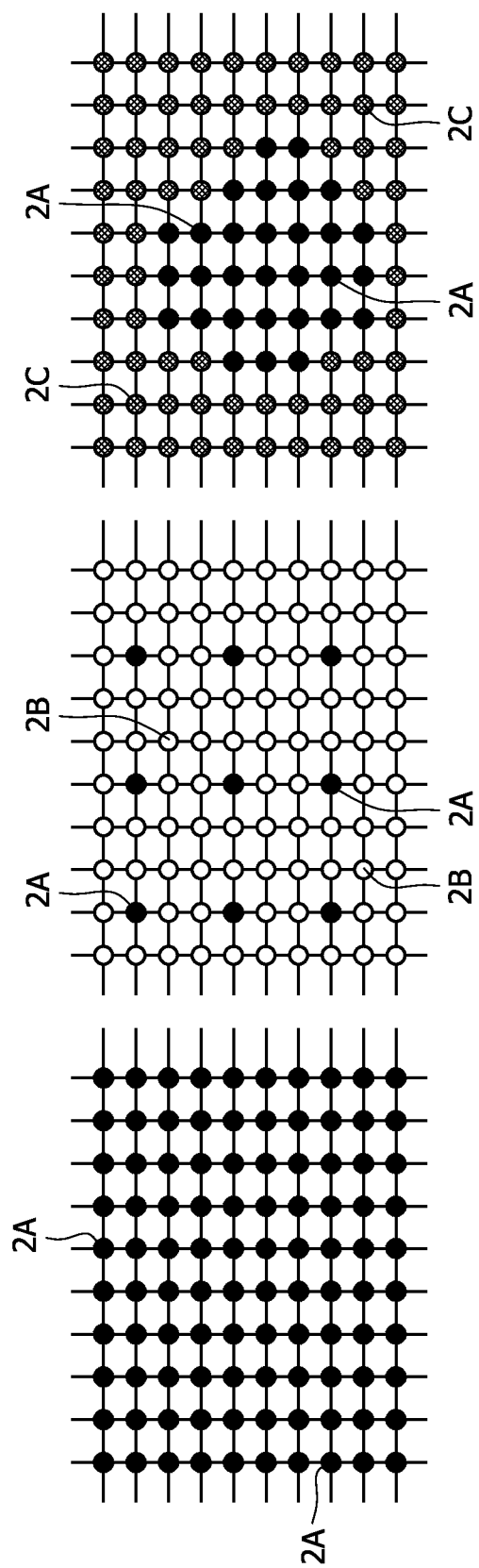

SKIN MONITORING DEVICE, METHOD OF MONITORING THE SKIN, MONITORING DEVICE, METHOD OF IRRADIATING THE SKIN, AND USE OF AN OLED

The invention relates to a skin monitoring device.

The invention also relates to a method of monitoring the color of the skin.

Furthermore, the invention relates to a color monitoring device.

Light, particularly IR and/or red light, is known to have beneficial effects on the human body such as, but not limited to, effective relief of muscular pains and stiffness of the joints; removal and/or reduction of bacteria, for example in ulcers or acceleration of wound repair; stimulating the fibroblasts into collagen production for stabilizing connective tissue and healing wounds, for example necrotic depths in burns; light-induced blood vessel and lymphe vessel vasodilation for possible aiding in cellulite treatment, acne and/or wrinkles; preventing and/or healing inflammation like eczema; healing of particular skin diseases; and more. The application of light, i.e., phototherapy, can shorten a stay in hospital after an accident or surgery, and the recovery, for example at home, can be accelerated. Aesthetic therapy, for example possible improvement of the skin, may also profit from phototherapy. Beneficial phototherapy devices provided with LEDs (Light Emitting Diodes) for emitting light to the skin are known.

Wound healing as well as other healing processes are often delicate and time-consuming processes, where careful monitoring of the skin is needed. Such a process may benefit from dedicated phototherapy wherein different types of light parameters like wavelength, pulse duration, intensity, etc. are applied to the wound during different stages of the healing process in time. A specific wavelength or other parameter may induce optimal stimulation of specific cells that are active at a certain time in the healing process. For example, different stages in wound healing may consist of collagen production, regeneration of vessels, and formation of the epidermis, which can be stimulated by specified wavelengths or other specified parameters.

Examples of beneficial intensities and/or other parameters for particular stages in the healing process are known in the art of phototherapy.

An object of the invention is to provide a convenient and efficient method of monitoring the state of the skin as a preparation for applying phototherapy.

This object and other objects are achieved by a skin monitoring device for use near the skin, comprising a processing circuit connecting means and at least one photosensor, wherein the at least one photosensor is configured to detect at least one approximate wavelength of light reflected and/or emitted by the skin, and wherein a signal receiving circuit is provided for receiving signals from the at least one photosensor.

The invention has identified the fact that information about the healing process of the skin can be found in the reflectivity and in some cases the emissivity of visible and non-visible light of the skin. Also, specialists can conveniently spend less time monitoring the patient thanks to the invention.

In an advantageous embodiment, ranges of wavelengths, i.e. approximate wavelengths, are detected with LEDs and/or OLEDs that function as photosensors. The reflectivity can be conveniently measured by measuring the signal that is output by the LEDs and/or OLEDs, wherein the degree of reflectivity is correlated to the strength of the measured signal.

In another embodiment, approximate wavelengths are detected with laser sensors, comprising lasers and photo sensors, the laser being adapted to allow a part of the laser beam to re-enter into the laser, and the photo sensor for measuring light emitted from the laser, thus obtaining a signal which varies in accordance with the interference between the original laser beam and the reflected laser beam. Such a laser sensor 19 is described in the international patent application WO2006/085278, for example. A laser sensor may allow for measuring in close proximity of the wound and more accurate wound healing monitoring.

In an embodiment in which the invention is integrated with or placed, for example, in or under a wound cover, the latter does not have to be changed frequently for monitoring the wound.

In specific embodiments, the state of a certain area of the skin is monitored while a phototreatment is being applied to the skin. After monitoring, skin data are delivered and specific parameters of light, for example the intensity thereof, can be adjusted locally. This may be done automatically, using a programmed algorithm, or by a specialist and in accordance with the measured skin data. Specific intensities and/or other parameters may be applied at a specific time.

In another embodiment, the skin monitoring device is provided with LEDs for emitting approximate wavelengths of light, particularly to apply phototherapy. These LEDs may also be configured to convert an approximate wavelength of light into a signal. In this embodiment, a phototherapy device and a skin monitoring device are integrated in a convenient way.

Said object and other objects are also achieved by a method of monitoring the skin by means of at least one photosensor that receives light that is reflected and/or emitted by the skin, wherein at least one, preferably at least two approximate wavelengths of light that are reflected and/or emitted by the skin are converted into at least one signal, and wherein the at least one signal is converted into skin data.

Furthermore, said object and other objects are achieved by a monitoring device comprising power source connecting means, at least one LED (Light Emitting Diode) or OLED (Organic Light Emitting Diode) for emitting as well as detecting at least one approximate wavelength, and a signal detecting circuit, wherein the LED or OLED is configured to have a detecting mode and wherein the signal detecting circuit is configured to detect signals that flow through the LED or OLED when the LED or OLED is in the detecting mode.

Furthermore, said object and other objects are achieved by a method of irradiating the skin by applying to said skin a monitoring device that monitors reflection and/or emission of light from said skin by means of at least one photo sensor, and emitting light to said skin by at least one LED or OLED, wherein the LED or OLED is controlled on the basis of signals from said at least one photo sensor.

Said object and other objects are also achieved by the use of a LED or OLED for registering light reflected or emitted by skin at a distance of between 0 and 5 mm.

FIGS. 3A, 3B and 3C are plan views of grids of LEDs according to an embodiment of a skin monitoring device;

In this description, identical or corresponding parts have identical or corresponding reference numerals. The exemplary embodiments shown should not be construed to be limitative in any manner and serve merely to illustrate the inventive concepts.

Figure 1:
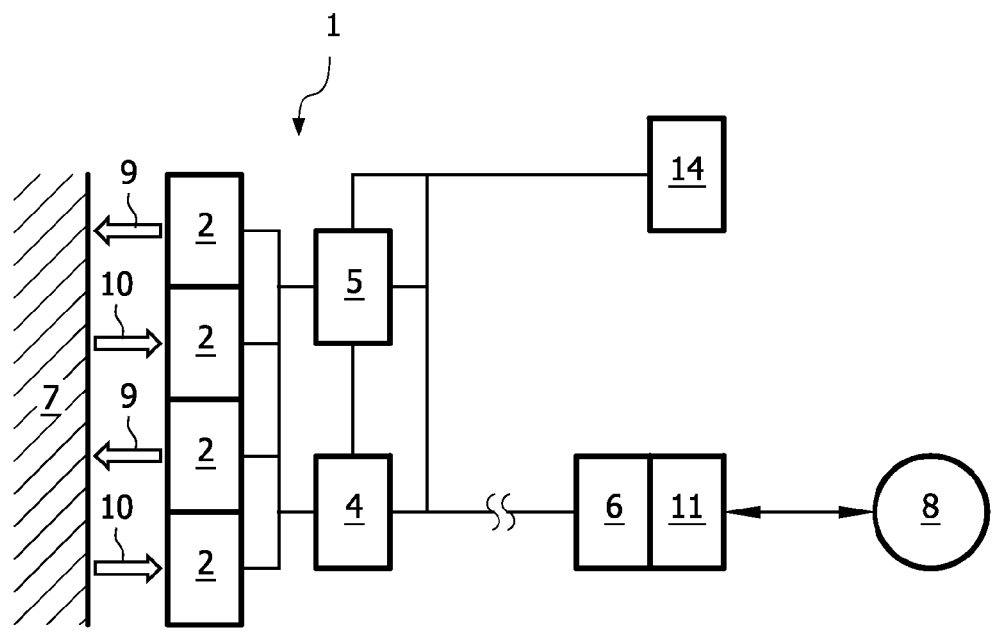
FIG. 1 is a diagram of an embodiment of a skin monitoring device.

A skin monitoring device 1 according to the invention is shown in FIG. 1. The skin monitoring device 1 is provided with LEDs (in this description: LEDs and/or OLEDs) 2 to measure the reflectivity and/or emissivity of the skin 7. The LEDs 2 convert the light 10 of an approximate wavelength/wavelength that is emitted and/or reflected by the skin 7 into a signal. Said 'approximate' wavelength has to be understood as a range of wavelengths, since neither a LED nor a photodiode emits and/or detects at an exact wavelength, but rather within a range of wavelengths that may vary. The approximate wavelength may vary, for example, within a short wavelength range of about 1 nm, several nm or tens of nm, for example 50 nm. Usually a LED has an emitting and/or detecting wavelength range of a few to a few tens of nanometers. A power supply 5 is provided to supply the LEDs 2 with power. Also, a frequency regulating circuit 14 is provided for pulsing the LEDs 2 with a certain frequency for noise and/or intensity control. The power supply 5 may also be connected to a signal receiving circuit 4, which picks up the signals and sends the signals to a processing circuit 6. In an embodiment, the processing circuit 6 reads the signals from a distance, for example with the aid of a wireless communication arrangement. The processing circuit 6 converts the received signals into skin data that are intelligible to a specialist 8 and/or can be read by a computer with the use of an interface 11. For example, by inspecting specific retrieved skin data on a user interface 11 the specialist 8 determines whether an adjustment in the healing process is needed. In another example, a computer applies an algorithm comparing the skin data with predetermined data and sends a signal to the light emitting device.

LEDs (Light Emitting Diodes) and/or OLEDs (Organic Light Emitting Diodes) can be configured to be light sources with certain temperature and constructional properties. They can be constructed so as to be relatively thin and free in shaping. This is in particular advantageous for obtaining a flexible light source that can cover a part of a patient's body with relatively little or no loss in freedom of movement for the patient. Furthermore, LEDs as well as OLEDs can be constructed to have control properties for varying parameters such as wavelength, brightness, color, pulse duration, intensity, heat emission, response time, etc. and can be made suitable to be fed by portable electrical current supply sources. These properties, such as a low heat emission, make both LEDs and OLEDs suitable as light sources for phototherapy purposes near the skin. For example, LEDs may be integrated in flexible materials such as, for example, woven and non-woven textiles, polymers, rubbery materials, foils, etc. For supplying power to and/or controlling the LEDs, these materials may be provided with conducting lines of an electrical circuit.

OLEDs are electroluminescent sources that can be configured to be flexible and/or transparent. OLEDs may either be small-molecule OLEDs and polymer OLEDs (polyLEDs). One OLED can cover a large area of the body without being interrupted while maintaining flexibility. The OLED covering said large area can be driven by just one set of electrodes. Obviously, several OLEDs may be combined into one lighting device. For both LED and OLED applications, extra layers may be added for light diffusion, cooling, protection of the light source, etc. In the description given below, any reference to LEDs may be construed as relating to LEDs and/or OLEDs, unless otherwise specified.

It is known that skin and/or elements thereof have a specific type of reflectivity/absorption at specific wavelengths that in turn corresponds to specific skin data. In this context, skin data is information that represents a specific state of the skin such as, for example, the degree of oxygenation of the blood, the redness of the skin, the melanin content in the epidermis, the amount of collagen, the elasticity and amount of elastin, and the amount of fat. Skin is defined as a layered structure of epidermis (c. 200 micrometer thickness), corium or dermis (c. 1-2 millimeter thickness), hypodermis or subcutaneous fat (of the order of mms-cms), muscles, cartilage, and bone. Water or moisture content, blood content, and degree of oxygenation of the blood are important parameters for measuring the state of the skin. These can be optically determined by measuring, for example, one and/or a combination of the wavelength-dependent absorption of skin chromophores, such as blood, melanin, carotenoids, flavins, etc; the wavelength-dependent scattering induced by refractive index changes at the cell membrane boundaries or at collagen fibres in the dermis; the wavelength-dependent scattering anisotropy (degree of angular dependence of the scattering); the wavelength-dependent refractive index, and the thickness of the layers. Therefore these specific states of the skin can be determined by a measurement of the reflectivity of the skin, which provides information on absorption and back scattering of the skin, at at least one, preferably two or more, wavelength(s) for certain elements of the skin at specific locations. Also, the skin emits thermal radiation in the mid-infrared spectral range (with a wavelength of 3 to 8 micrometers) which can serve as a measure for the skin's temperature based on the relation with water absorption bands in this wavelength range.

Figure 2A:
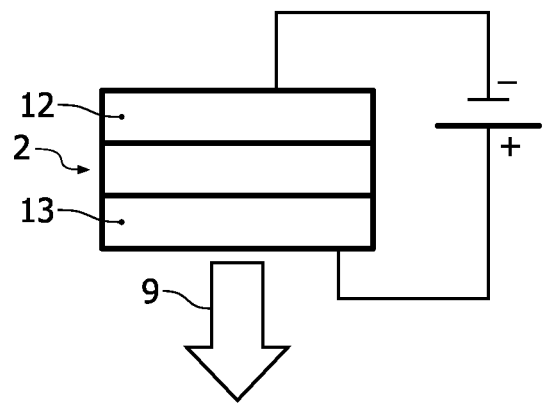
FIGS. 2A and 2B are schematic side elevations of a LED according to an embodiment of a skin monitoring device.
Figure 2B:
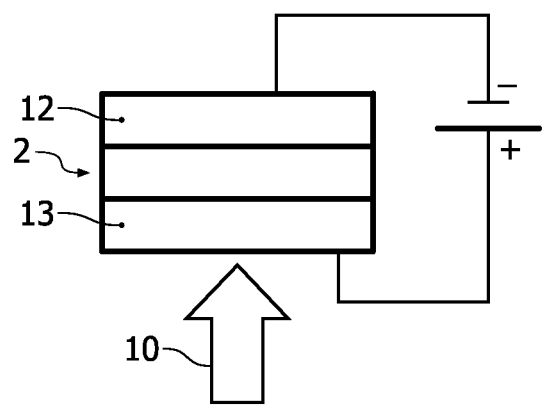

As is known from the art and illustrated in FIG. 2A, LEDs 2 emit light 9 at an approximate wavelength when electrons move from a conduction band 12 into a valence band 13. The approximate wavelength varies, for example within a spectrum band by several nanometers or several tens of nanometers. As is illustrated in FIG. 2B, the LED 2 functions as a photosensor in the reverse direction, i.e. light 10 of a specific wavelength range excites electrons from the valence band into entering the conduction band, producing a current when a voltage is applied. Thus, LEDs 2 are suitable for emitting light 9 by means of a current as well as for receiving light 10 so that a current is provided. A high reflectivity and/or emissivity of light by the skin will normally cause a higher current. During use the signal receiving circuit 4 detects the amount of current that is activated by a specific light receiving LED 2, so that the reflectivity and/or emissivity can be determined, at least approximately, from the characteristics of the LED 2.

In principle, photosensors 2 other than LEDs 2 are also suitable for detecting light, for example photodiodes and/or lasers. These alternative photosensors are preferably provided in a substantially flat and/or flexible monitoring device 1 for use near the skin. Examples of fields of application for the photosensors 2 include, but are, not limited to, bruise age detection, skin flap viability, microcirculation, port wine stain removal treatment monitoring, dermatologic disorder monitoring, and efficacy of photodynamic therapy.

Although the quality and function of LEDs 2 are regarded as less preferable in practice than those of photosensors such as, for example, lasers and/or photodiodes, the characteristics of LEDs 2, such as the fact that they can be configured to be flexible, make their application convenient in fields such as inter alia phototherapy and/or flexible light source applications. Moreover, LEDs 2 can be configured to function both as light emitters and as detectors.

According to an embodiment, the skin 7 reflects light 10 originating from a light source back as light 9. In different embodiments, the light source may comprise instead of LEDs 2, for example, natural light, a laser light source and/or other light sources that are known, specifically in the field of phototherapy.

In advantageous embodiments, light 9 is emitted as well as detected by LEDs 2. The construction of such a skin monitoring device 1 can be kept relatively simple and flexible. Furthermore, it is possible to map the reflectivity of the skin, since the use of multiple LEDs 2 allows the reflectivity of the skin to be measured at different locations, where different degrees of reflectivity can be measured. The reflectivity can be measured for different locations and/or areas of the skin and sequentially in time, such that the emitted light is adjusted in time, if so required. This is also illustrated in FIGS. 3A to 3C.

FIG. 3A shows a grid of LEDs 2A that are turned on to stimulate wound healing. As is illustrated in FIG. 3B, the skin reflectivity is measured at certain time intervals, using LEDs 2B that are in a light detecting mode for detecting the reflectivity, while LEDS 2B function as photosensors generating a photocurrent and LEDs 2A function as light emitters. The current excited by the light received by the LED 2B is received by a signal receiving circuit 4 and processed to be converted into skin data. Since the skin monitoring device 1 can be configured such that the LEDs 2 are close to the skin 7, the reflectivity can be measured as a function of the location. In principle, the LEDs 2 can be laid against the skin 7. In other embodiments, the LEDs 2 emit and/or detect light at a small distance from the skin 7, for example of about several mm.

If, for example, an inflammation of the skin is concluded from a local reddening of the skin and a corresponding local difference in reflectivity from the surrounding skin, the processing circuit 6 will provide a signal, for example to a computer circuit, a user interface 11, and/or a specialist 8. This measuring procedure can be repeated with turned on LEDs 2A and detecting LEDs 2B in various positions. In this way a mapping of the skin 7 can be made in the form of skin data, which can be used to stimulate wound healing more effectively, as shown in FIG. 3C. For example, the intensity of the LEDs 2C is adjusted as a function of their location above the skin 7. Here, all LEDs 2A, 2C are emitting light, but the LEDs 2C have another intensity than the LEDs 2A. Of course, a gradient of light intensities can be applied across the grid of LEDs 2, where the intensity varies gradually across the grid.

In an advantageous embodiment, the LEDs 2A, 2C emit light at a pulsed frequency provided by a frequency regulating circuit 14. The pulsed frequency turns the emitted light on and off, enabling noise such as scattering to be filtered by the processing circuit 6 and an algorithm. A higher signal to noise ratio can be obtained with the use of the frequency regulating circuit 14.

In an embodiment of the invention, in principle all or most LEDs 2 that are incorporated in the skin monitoring device 1 are configured to emit as well as detect light. In this embodiment, one LEDs 2 is configured to have a light detecting mode at specific time intervals and a light emitting mode at other time intervals. In another embodiment, specific LEDs 2 are configured to emit and other LEDs are configured to detect light.

In an embodiment, instead of and/or next to LEDs 2, lasers 16 are used for irradiating the skin 7. The irradiated light may penetrate relatively deep under the surface of the skin 7, e.g. up to several mms and/or cms, e.g. for monitoring blood perfusion in tissue below the skin. A photo sensor 17 detects the light that is scattered by the skin 7 and/or by the tissue below the skin surface, e.g. blood cells. A sensor comprising both said laser 16 and photo sensor 17 is referred to as laser sensor 19 in this description. In a preferred embodiment the laser sensor 19 is provided with a lens 18 for focusing the light from said laser 16.

Figure 1A:
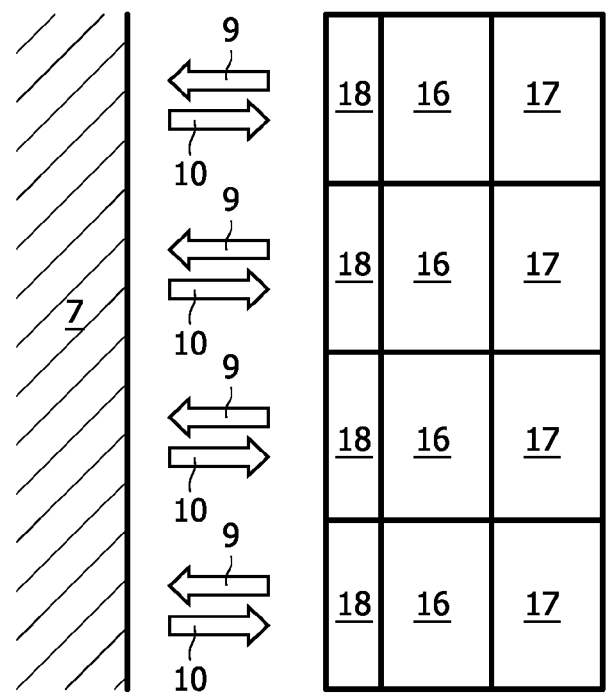
FIG. 1A is a diagram of another embodiment of a skin monitoring device.

An embodiment having a laser sensor 19 is illustrated in FIG. 1A, wherein the laser 16 is arranged to illuminate the tissue 7 in such a way that a portion of the light beam 10 that is scattered by the tissue re-enters the laser 16 in order to obtain a self-mixing effect. Such a laser sensor 19 is described in the international patent application WO2006/085278, the content of which is herein incorporated by reference. A more general type of self-mixing laser sensor comprising a laser and a photo sensor is described in WO02/37410. The light 10 that is reflected by the tissue and registered as an electrical signal by the photo sensor 17 contains a signal that varies in accordance with the interference between the original laser beam and the scattered laser beam. Since each single blood cell will produce a signal with a Doppler shift with respect to the outgoing laser beam, which shift depends on that blood cells velocity in the direction of the laser beam, this signal can be used for monitoring tissue and is particularly useful for measuring data such as the relative amount of blood cells, the average velocity of blood cells, the blood perfusion and/or related blood characteristics. The Doppler shifts will produce a speckle pattern, which is the sum of a large number of sinusoidal functions. Preferably, the processing circuit 6 is adapted to apply a Fourier transform to said signal in order to provide the spectrum of the signal, and to apply an exponential fit to said spectrum, thereby obtaining parameters corresponding to the average blood cell velocity in the tissue and the amount of blood in the tissue.

The laser sensor 19 is, like LEDs 2 suitable for miniaturization and can e.g. be integrated in flexible materials such as, for example, bandage, woven and non-woven textiles, polymers, rubbery materials, foils, etc. In use the distance between the laser sensor 19 and the skin 7 can be kept advantageously small, e.g. between 0 and 2 mms, in particular when a lens 18 is provided in the device the lens 18 may be in direct contact with the skin 7. Because of the improved coherence of the laser light with respect to LEDs 2, e.g. in a wavelength range of between one (or less) and a few nms, its light is particularly useful for measuring and comparing the scattered light with the irradiated light. Furthermore the embodiment comprising said laser 16, photo sensor 17 and/or lens 18, can be particularly useful for measuring blood flow, which is particularly useful for monitoring the wound, such that measurements can be taken to expedite the healing process. Moreover, the blood perfusion may be a more reliable parameter for monitoring the recovery of a wound that skin reflectivity, such that the laser sensor 19 can be relatively accurate, e.g. more accurate than LEDs 2. However, a laser sensor 19 could also be used for measuring skin reflectivity or another parameter, in which case for example the focal length of the lens 18 can be adapted.

In a practical embodiment of a monitoring device 1, some or all LEDs 2 are replaced by laser sensors 19. A first embodiment comprises a grid of LEDs 2 (FIG. 3D), wherein several LEDs 2 are replaced by laser sensors 19. With this combined monitoring device 1, for example the skin colour as well as the blood perfusion can be measured, preferably by means of the LEDs 2 and the laser sensor 19, respectively. Combined monitoring may provide for relatively detailed information on the wound healing process, wherein local information at several location with respect to the tissue can be obtained. Furthermore, the laser sensors 19 may aid in improved measuring of the scattered light and comparing of the scattered light with the irradiated light, because of the higher coherence of the laser light with respect to the LEDs 2 in a detection mode, whereas the irradiated light of the LEDs 2 may have the same healing effect as that of the lasers 16. The lasers 16 may also aid in irradiating tissue for healing. The lasers 16 and/or the LEDs 2 could for example be configured for different types of dedicated healing, for example the lasers 16 having different frequencies and/or wavelengths than the LEDs 2. This may also be achieved by adapting the focal length of different lenses 18, for example.

Figure 3D:
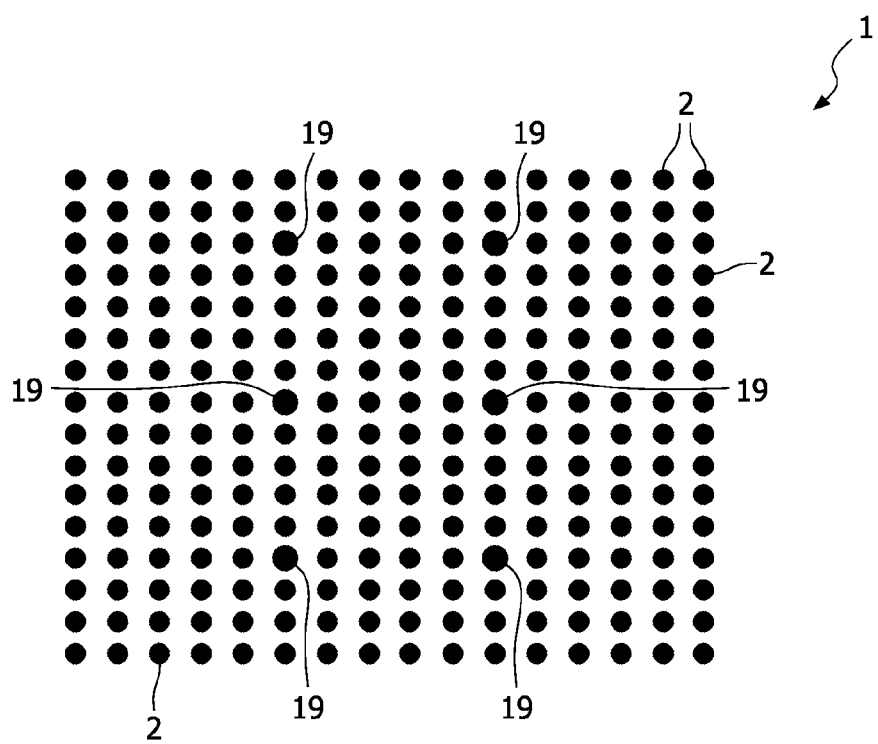
FIG. 3D is a plan view of a grid of LEDs and laser sensors according to an embodiment of a skin monitoring device.
Figure 3E:
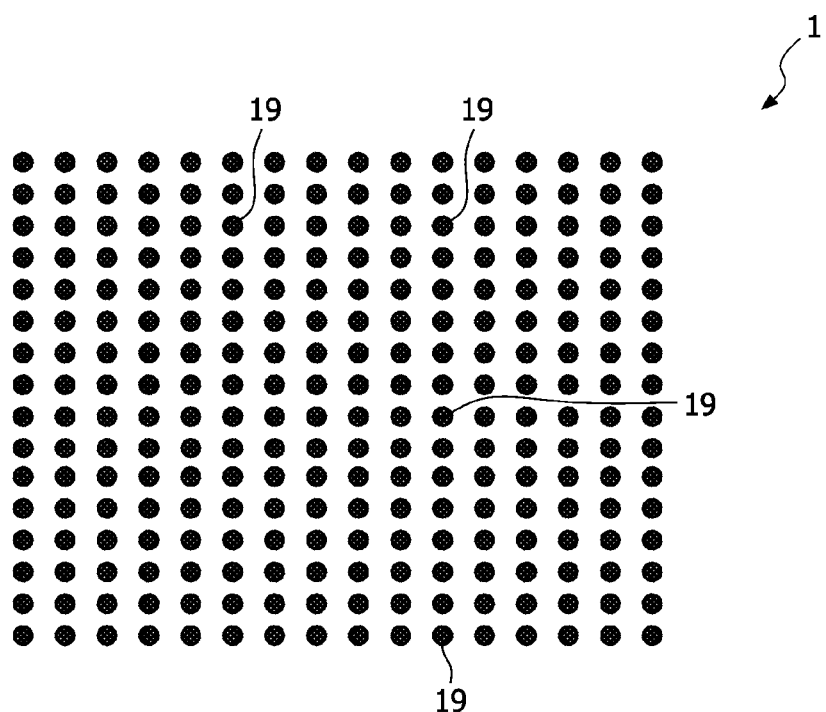
FIG. 3E is a plan view of a grid of laser sensors according to an embodiment of a skin monitoring device.

In FIG. 3E an embodiment is shown of a monitoring device 1 with a grid of laser sensors 19. In this embodiment, a higher monitoring resolution as compared to the embodiment of FIG. 3D can be obtained, wherein the lasers 16 may also be used for healing.

Depending on the local signal that is measured by the different LEDs 2 and/or laser sensors 19 the light that is emitted by the lasers 16 and/or LEDs 2 can be adjusted locally to optimize the treatment. For example, in use multiple laser sensors 19 are provided at different locations with respect to the surface of a wound such that the signal can be measured locally and/or the amount of radiation is adjusted locally.

The combined grid, e.g. as shown in FIG. 3D, or the laser sensor 19 grid, e.g. as shown in FIG. 3E, can for example be conveniently embedded in flexible material such as textile or bandage. Preferably the laser sensors 19 are embedded in material that can be conveniently worn near the body, since laser sensors 19 can be situated near the body, for example 2 mms or less from the skin, or can be in contact with the body. Connecting a laser sensor 19 to such flexible material may be similar to connecting a LED 2 to such flexible material.

As mentioned above, the laser sensors 19 may be provided with lenses 18. In the same way, the lenses 18 may be provided for other light sources, such as LEDs 2, e.g. in other embodiments of the invention. The lenses 18 may have a focal length that is optimized for a pre-specified treatment. For example, when blood cell characteristics are to be measured, a lens 18 may have a focal length of 2 mm or less, e.g. 1 mm. It may also be convenient to apply different lenses 18 having different focal lengths, such that in use the tissue is monitored at different depths by the same monitoring device 1.

In an advantageous embodiment, the color that is reflected by an area of the skin 7 is detected in that the reflectivity of the area of the skin is detected at at least two different emitted wavelengths. More specifically, a more accurate detection of the reflectivity of the skin 7 is achieved in that the ratio is calculated between the two obtained signals that correspond to two corresponding approximate wavelengths of emitted LED light. In the art, predetermined tables are known that plot ratios of reflectivity of the skin at different wavelengths against specific skin data, for example redness of the skin, temperature of the skin, etc. The measurements may even be more accurate if more than two wavelengths are used. For the sake of clarity, this description will generally refer to two wavelengths, although more than two wavelengths may also be applied according to the invention.

For measuring the amount, perfusion and/or velocity of blood, e.g. by means of laser sensors 19 or other light sources, there may be no need to measure the colour of the skin. Therefore emitting at one wavelength may be sufficient. In this case the different scattered signals of different blood cells are measured and compared with respect to one location. From the resulting speckle pattern the information about the amount, perfusion and/or velocity of blood can be obtained.

Figure 4:
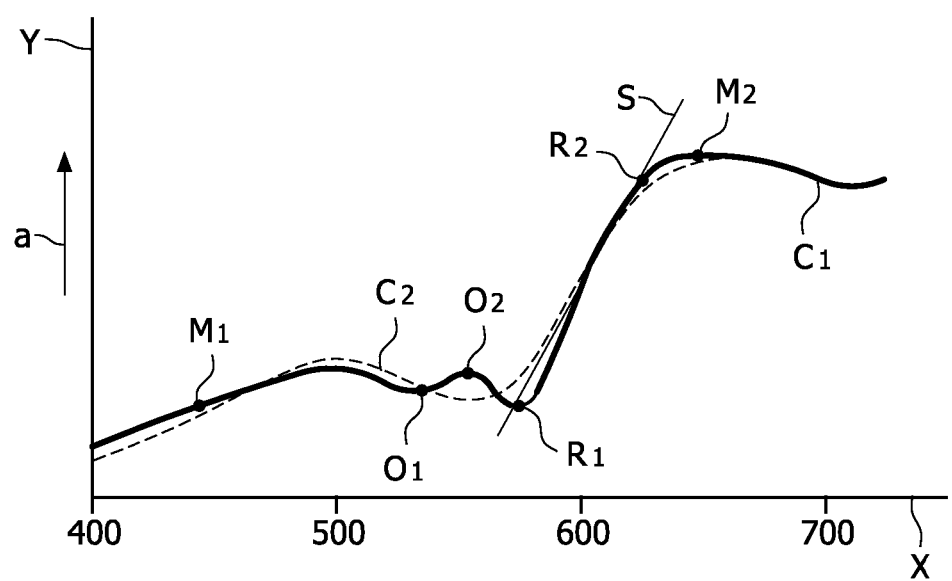
FIG. 4 shows two curves wherein the wavelength is a function of the reflectivity.

In an exemplary embodiment, an estimate of the redness of the skin 7 can be determined by calculating the above-mentioned ratio of the reflectivity at two different emitted wavelengths, for example in the visible wavelength range. The reflectivity is detected by the LEDs 2 functioning as photosensors and converted into a signal. In FIG. 4, the reflectivity of the skin of one person is plotted on a vertical axis Y, the reflectivity increasing in upward direction, indicated with an arrow A. The wavelengths that are emitted to the skin of this person by the at least one LED 2 are plotted on a horizontal axis X in nanometers. A curve $C_1$ is drawn which indicates the measurements of the skin reflectivity at different wavelengths. In FIG. 4 the curve is plotted in the visible wavelength range, from about 400 to about 820 nm. In this example the redness of the skin can be determined by measuring the reflectivity, or the signals thereof, at a wavelength of approximately 580 nm and 620 nm, shown in FIG. 4 as dots $R_1$ and $R_2$, respectively. A slope between the dots $R_1$ and $R_2$ is indicated by a straight line S through the dots $R_1$ and $R_2$, which slope is defined by the reflectivity $R_2$ minus the reflectivity $R_1$ divided by the difference in wavelength 620-580 nm=40 nm. Here, the ratio $R_1/R_2$ is also a measure for the redness, a lower value corresponding to more redness. The ratio between the signals is determined such that specific skin data, in this example the redness of the skin 7, can be retrieved from said predetermined tables or other predetermined data, for example with the aid of a processing circuit 6 or by a doctor. In a less sophisticated embodiment, a specialist 8 translates the detected signals into skin data himself, for example with the aid of a handbook.

In an exemplary embodiment, the degree of oxygenation of blood, particularly capillary blood, can also be determined by detecting the reflectivity of the skin at two or more wavelengths. In this embodiment it is advantageous to detect the reflectivity at an approximate wavelength wherein the reflectivity, i.e. light absorption, of hemoglobin and oxyhemoglobin is approximately the same, i.e. at an isobestic point, and at at least one other approximate wavelength where the reflectivity values of hemoglobin and oxyhemoglobin are different. Detection of the reflectivity of the skin 7 at a relatively high level of oxyhemoglobin and at a relatively high level of hemoglobin leads to curve $C_1$ and dotted curve $C_2$, respectively. The two curves cross at an isobestic point $O_1$, whereas different reflectivities are obtained at dot $O_2$. The ratio of the two reflectivities at $O_1$ and $O_2$ is a measure for the oxygenation degree. Generally the oxygenation degree in wounds is smaller than in normal tissue. However, the microcirculation may differ locally, and wound oxygenation may vary from one anatomical position on the body to another, which may be taken into account. The position on the body may therefore also serve as a reference for the wound oxygenation.

In a further exemplary embodiment, the melanin content in the skin can be measured. The slope of the reflectance spectrum is a measure for the melanin content, i.e. the fairness or darkness of the skin. For fair skin the slope is relatively high, for dark skin the slope is relatively low. For example, a signal at about 450 and about 660 nm can be measured, indicated in FIG. 4 with dots $M_1$ and $M_2$, respectively. For example, the relative difference in signal strength at these wavelengths, normalized to the signal at 660 nm, is a measure for the melanin content. Since melanin content may vary locally (e.g. birthmarks) or between persons, the measured melanin content may be used to compensate for the measured reflectivity of other characteristics, for example when determining the redness of the skin.

In another exemplary embodiment, skin reflectivity is dependent on skin moisturization. This can be measured in the near-infrared region, for example at water absorption bands of between approximately 1450 and/or approximately 2000 nm. The skin exudates (moisturization) can give an indication of the state of a wound, for example whether it is open, i.e. relatively wet, or closed, i.e. relatively dry.

In another exemplary embodiment, the emissivity of the skin is measured, for example by detecting longer-wavelength radiation in the infrared region, for example in a range between approximately 2500 and 8500 nm. The emissivity, particularly in said range, is related to the temperature of the skin and can give an indication of inflammation, since the skin temperature is generally increased at an inflamed area.

Of course, in other embodiments the reflectivity and/or emissivity is detected at different wavelengths than the abovementioned wavelengths and for different skin data than in the abovementioned exemplary embodiments. The numbers and ranges of wavelengths given above are not to be regarded as limiting the invention in any way. They merely serve as illustrative examples. More advantageous wavelengths may be known in the art and may change in practice as research in this field continues, while predetermined data used in algorithms are to be updated continuously.

In other embodiments, the skin monitoring device is configured to combine the different abovementioned skin monitorings. The skin monitoring device 1 is configured, for example, to detect characteristics like melanin content, skin redness, temperature, oxygenation, and moisturization, or at least two of those, wherein the characteristics may be interdependent. In such an embodiment it is advantageous if the LEDs 2 emit and/or detect at more than two wavelengths.

As was mentioned above, it is advantageous in particular embodiments to have the skin monitoring device 1 emit light at at least two different wavelengths in approximately the same location and/or area. It is advantageous for this purpose to have LEDs 2 emit in at least two different wavelength ranges. Therefore, advantageously, different types of LEDs 2 may be used, each type emitting and detecting within a specific wavelength range. The wavelength and/or intensity of the LEDs 2 can be controlled locally, for instance individually and/or in groups of LEDs 2. The wavelength may be varied, for example, by turning different LEDs 2 of different wavelengths on and off. Different LEDs 2 may, for example, be situated close to each other and/or stacked so as to be able to control and monitor the emitted LED light relatively accurately at specific locations for different approximate wavelengths that are emitted and/or reflected by the skin 7. Techniques are also known in which a single type of LED 2 emits and/or detects at different wavelengths.

Figure 5:
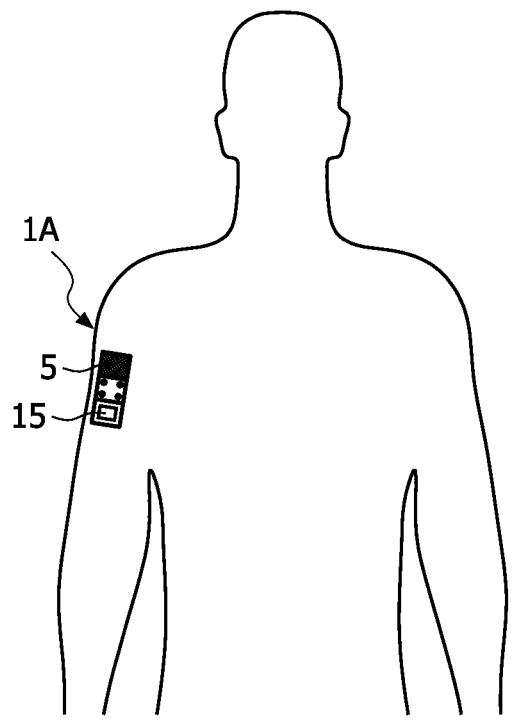
FIG. 5 shows a drawing of an embodiment of a skin monitoring device that is integrated in a plaster.
Figure 6:
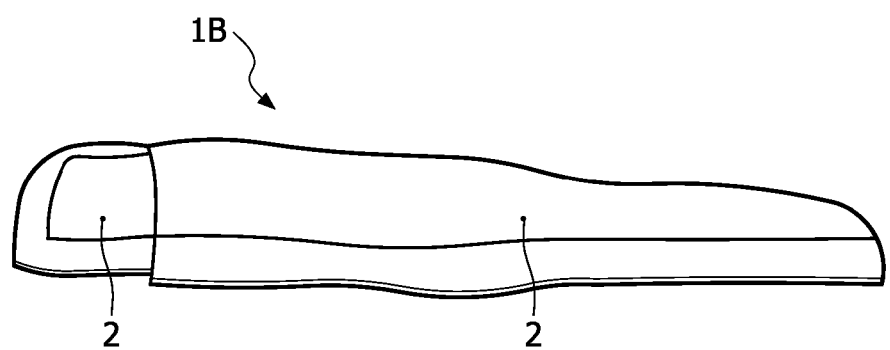
FIG. 6 shows a drawing of an embodiment of a skin monitoring device that is integrated in a blanket.

In an advantageous embodiment, the skin monitoring device 1 is flexible, or can at least conform to a part of a body, to provide a certain amount of freedom of movement. In an embodiment, the LEDs 2 are integrated into a body cover, like a plaster 1A, bandage, clothes, blankets 1B, etc., so as to be worn on and/or around the body, see FIGS. 5 and 6. The skin monitoring device 1 may be substantially flat, for example for wearing underneath clothes and/or blankets. FIG. 5 shows that a portable and/or disposable power supply 5 is connected to the skin monitoring device 1. A transmitter 15 or some other wireless communication unit may be arranged and configured to transmit signals to the processing circuit 6. FIG. 6 shows an embodiment of a blanket 1B with flexible OLEDs 2.

In another embodiment, the LEDs 2 are kept at a distance from the wound, i.e. not touching the wound, to prevent inflammation. For example, the LEDs 2 may be kept at a distance of approximately 0.1 mm up to approximately 50 mm from the skin and/or wound, preferably between approximately 2 and 30 mm, for example to allow enough air to pass by the wound. For the same reasons at least part of the material of the skin monitoring device 1 may be configured to be breathable and/or absorbing. The skin monitoring device 2 may comprise spacers to set this distance. These spacers may comprise, for example, dots of adhesive, a soft porous layer, a gauze, etc.

In an advantageous embodiment, the skin monitoring device 1 comprises a wireless communication arrangement for communication with a distant computer and/or specialist 8. The specialist 8 and/or computer can monitor the healing process from a distance and adjust the intensity and/or wavelength of the LED light 9, if so desired. In an embodiment, the skin monitoring device 1 is configured to have the patient monitor the healing process and handle the skin monitoring device 1, such that he or she can adjust the settings of the skin monitoring device 1 him/herself, for example by means of a user interface 11. The processing circuit 6 and the user interface 11 can be configured to interact in the healing process automatically and/or to warn the patient and/or specialist if interaction is needed.

Obviously, instead of a separate signal detecting circuit 4 and frequency regulating circuit 14, the processing circuit 6 may be configured such that it encompasses a signal detecting circuit 4 and/or a frequency regulating circuit 14. It or they may also be directly connected to the lighting device.

Furthermore, the principle of the invention may be applied outside the field of phototherapy. For example, light that is reflected from surfaces in general can be measured with a skin monitoring device 1 according to the invention. This might be advantageous for studying, for example, certain materials and/or biological lifeforms. For example, one can measure the reflectivity of surfaces with relatively easy means by using multiple LEDs 2 as light emitting as well as light detecting sources.

It will be obvious that the invention is not limited in any manner to the exemplary embodiments presented in the description and the drawings. Many variations are possible within the scope of the invention as outlined by the claims. A skin monitoring device 1 may be configured, for example, for any type of phototherapy, not specifically or exclusively for the applications described in the above text. Combinations of two or more aspects of the embodiments or combinations of the embodiments are possible within the scope of the invention. All comparable variations are understood to fall within the scope of the invention as outlined by the claims.

The invention claimed is:

1. A skin monitoring device for application near a skin, comprising:
   a plurality of light units each having an emitting mode for emitting light towards the skin and a detecting mode for detecting at least one approximate wavelength of light reflected by the skin;
   a signal receiving circuit configured to receive a first signal from a first light unit of the plurality of light units and a second signal from a second light unit of the plurality of light units operating in the detecting mode, and to determine an amount of current excited by the light received by the first light unit and the second light unit; and
   a processing circuit configured to convert the determined amount of the current into skin data by comparing the determined amount of the current with reference current values associated with predetermined skin data, and to selectively operate the plurality of light units in the emitting mode and the detecting mode to generate a map of the skin using the skin data;
   wherein the first light unit includes a first fixed lens and the second light unit includes a second fixed lens, the first fixed lens having a first fixed focal length for a pre-specified treatment of the skin at a first depth of a desired location and being configured to directly receive light emitted directly from the first unit and to focus the light emitted directly from the first unit onto the first depth, and the second fixed lens having a second fixed focal length different from the first fixed focal length for the pre-specified treatment of the skin at a second depth different from the first depth and being configured to focus light directly from the second unit onto the second depth of the desired location,
   wherein the light emitted from the first unit has a frequency and the light emitted from the second unit has the same frequency and the difference in depth between the first and second depths results from the first and second fixed lenses having different fixed focal lengths;
   wherein the map comprises a map of reflectivity of the skin, and the processing circuit is configured to adjust intensities of the plurality of light units based on the map and as a function of locations of the plurality of light units above the skin.

2. The skin monitoring device according to claim 1, wherein the plurality of light units, in the emitting mode, is configured to emit light of at least two approximate wavelengths of light.

3. The skin monitoring device according to claim 1, wherein the plurality of light units comprises a laser.

4. The skin monitoring device according to claim 1, wherein the plurality of light units include a laser as a light source for illuminating the skin, the laser being adapted to allow a part of a laser beam, scattered by the skin, to re-enter into the laser, and a photo sensor for measuring light emitted from the laser for obtaining a signal which varies in accordance with an interference between an original laser beam and a scattered beam scattered by the skin.

5. The skin monitoring device according to claim 4, wherein the skin monitoring device is configured to emit and/or detect light at a distance of between 0 and 2 mms from the skin.

6. The skin monitoring device according to claim 1, wherein the plurality of light units comprises at least one of a light emitting diode and an organic light emitting diode.

7. The skin monitoring device according to claim 1, wherein the plurality of light units comprises a light emitting diode, an organic light emitting diode, and laser sensors.

8. The skin monitoring device according to claim 1, which is configured to conform at least partly to the shape of a human body, and is configured to be at least partly flexible.

9. The skin monitoring device according to claim 1, further comprising at least one spacer such that the skin monitoring device emits and/or detects light at a distance from the skin of between approximately 0.1 and 50 mm.

10. The skin monitoring device according to claim 1, further comprising a storage arrangement for storing the predetermined skin data.

11. The skin monitoring device according to claim 1, further comprising a wireless communication arrangement for communication between the signal receiving circuit and the processing circuit.

12. The skin monitoring device according to claim 1, wherein the processing circuit is further configured to adjust intensity of light emitted by a portion of the plurality of light units operating in the emitting mode based on light detected by a part of the plurality of light units operating in the detecting mode.

13. The skin monitoring device according to claim 1, further comprising at least one spacer such that the skin monitoring device emits and/or detects light at a distance from the skin of between approximately 2 and 30 mm.

14. The skin monitoring device according to claim 1, wherein the processing circuit is further configured to determine the skin data from a ratio of at least two signals that are converted at at least two different wavelengths of the light reflected by the skin.

15. The skin monitoring device according to claim 1, wherein the processing circuit is further configured to convert light sequentially into signals relating to different locations of the skin.

16. The skin monitoring device according to claim 1, wherein the plurality of light units includes light units that are stacked over one another.

17. The skin monitoring device of claim 1, wherein the processing circuit is further configured to use the map to gradually adjust intensities of the plurality of light units as a function of locations of the plurality of light units above the skin.

18. The skin monitoring device of claim 1, wherein the processing circuit is further configured to automatically provide an indication that a user interaction is needed.

19. A method of operating a skin monitoring device, comprising acts of:
   emitting light towards the skin by a plurality of light units in an emitting mode;
   detecting by the plurality of light units in a detecting mode, at least one approximate wavelength of light reflected by the skin;
   receiving in a signal receiving circuit, a first signal from a first light unit of the plurality of light units and a second signal from a second light unit of the plurality of light units operating in the detecting mode, and determining an amount of current excited by the light received by the first light unit and the second light unit; and converting by a processing circuit, the determined amount of the current into skin data by comparing the determined amount of the current with reference current values associated with predetermined skin data, and selectively operating the plurality of light units in the emitting mode and the detecting mode to generate a map of the skin using the skin data, wherein the act of emitting light includes acts of:

emitting a first light from the first light unit through a first fixed lens; and emitting a second light from the second light unit through a second fixed lens, the first fixed lens having a first fixed focal length for a pre-specified treatment of the skin at a first depth of a desired location and directly receiving light emitted directly from the first unit and focusing the light emitted directly from the first unit directly onto the skin at the first depth, and the second fixed lens having a second fixed focal length for the pre-specified treatment of the skin at a second depth different from the first depth and directly receiving light emitted directly from the first unit and focusing the light emitted directly from the second unit directly onto the skin at the second depth of the desired location, wherein the first emitted light has a frequency and the second emitted light has the same frequency, and the difference in depth between the first and second depths results from the first and second fixed lenses having different focal lengths, wherein the map comprises a map of reflectivity of the skin, and adjusting the intensities of the plurality of light units by a processing circuit according to the map and as a function of locations of the plurality of light units above the skin.

* * * * *